United States Patent [19]

Smith, Jr.

[11] 4,375,576
[45] Mar. 1, 1983

[54] ENHANCED DIISOBUTENE PRODUCTION IN THE PRESENCE OF METHYL TERTIARY BUTYL ETHER

[75] Inventor: Lawrence A. Smith, Jr., Bellaire, Tex.

[73] Assignee: Chemical Research & Licensing Co., Houston, Tex.

[21] Appl. No.: 287,193

[22] Filed: Jul. 27, 1981

[51] Int. Cl.³ .............................................. C07C 2/04
[52] U.S. Cl. ................................ 585/510; 585/515; 585/526; 585/820; 585/830; 585/832
[58] Field of Search ............... 585/510, 800, 832, 921, 585/830, 820, 515, 526

[56] References Cited

U.S. PATENT DOCUMENTS

| | | | |
|---|---|---|---|
| 4,071,567 | 1/1978 | Ancillotti et al. | 585/510 |
| 4,215,011 | 7/1980 | Smith | 585/510 |
| 4,218,569 | 8/1980 | Chase et al. | 585/832 |
| 4,242,530 | 12/1980 | Smith | 585/510 |
| 4,313,016 | 1/1982 | Manning | 585/832 |

OTHER PUBLICATIONS

Haag, Kinetic & Catalysis, #73 vol. 63, pp. 140–147.

Primary Examiner—Delbert E. Gantz
Assistant Examiner—Asokkumar Pal
Attorney, Agent, or Firm—Kenneth H. Johnson

[57] ABSTRACT

In the liquid phase reaction of isobutene in the presence of resin cation exchange resins with itself in a $C_4$ hydrocarbon stream to form dimers, the formation of higher polymers, oligomers, and co-dimer by-products is suppressed by the presence of 0.0001 to 1 mole per mole of isobutene of methyl tertiary butyl ether.

13 Claims, 1 Drawing Figure

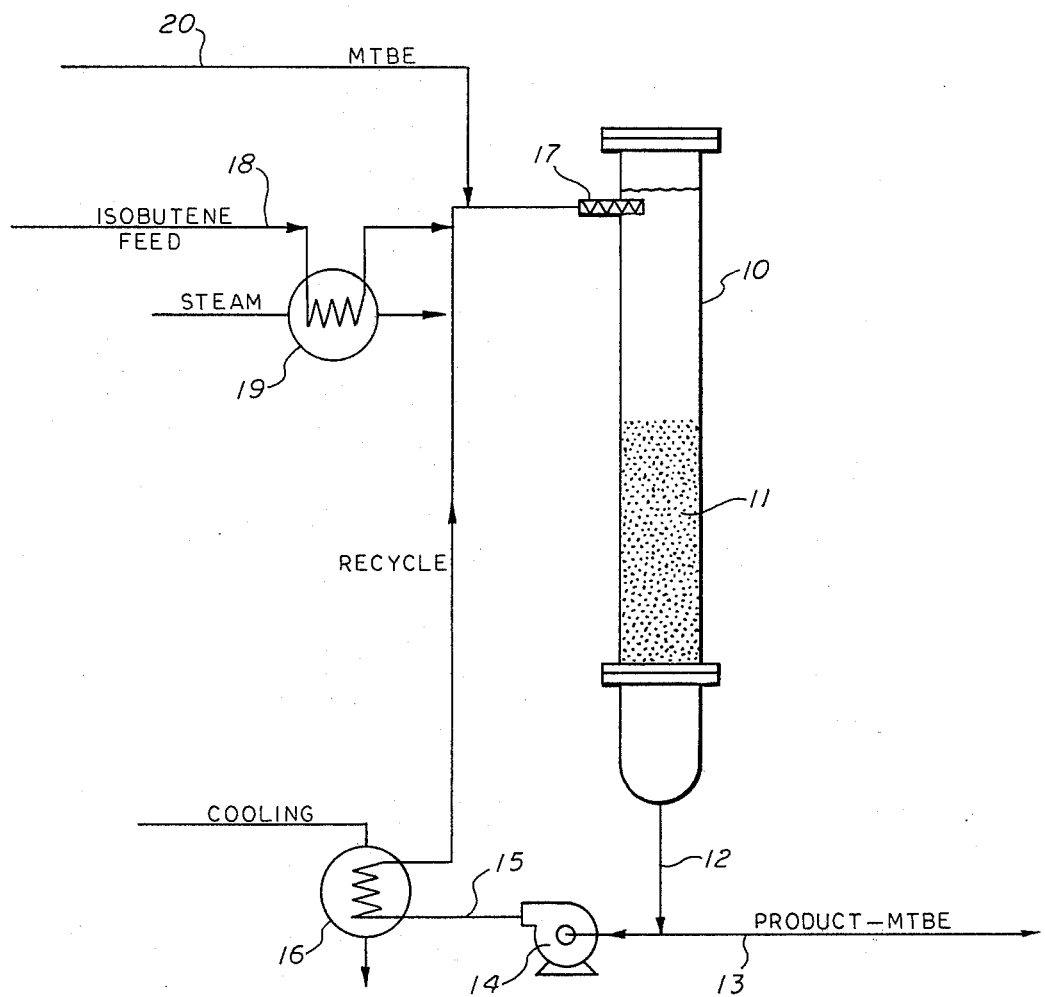

ENHANCED DIISOBUTENE PRODUCTION IN THE PRESENCE OF METHYL TERTIARY BUTYL ETHER

The Government of the United States of America has certain rights in this invention pursuant to Contract No. DE-FC07-80CS40454 awarded by the U.S. Department of Energy.

BACKGROUND OF THE INVENTION

1. Field of the Invention

The present invention relates to the separation of isoolefins from streams containing mixtures of an isoolefin and the corresponding normal olefin. The present invention is especially useful for the separation of isobutene from streams containing n-butenes by oligomerizing the isobutene. More particularly, the present invention results in a higher diisobutene production and less of the higher oligomers or polymers.

2. Prior Art

Isoolefins of four carbon atoms are difficult to separate from the corresponding normal olefin by simple fractionation because of the closeness of their boiling points. In prior art processes as generally practiced commercially, the isoolefin is selectively absorbed by sulfuric acid and the resulting isoolefin-containing sulfuric acid extract is then diluted and heated or treated with steam to separate the isoolefin.

Isobutene and diisobutene are of significant value having diverse applications, for example, isobutene is one of the comonomers for butyl rubber and diisobutene is an intermediate in the preparation of detergents. The isobutene oligomers are useful as polymer gasoline. The n-butenes are required in pure form for homopolymerization and as feeds for the oxidative production of butadiene. One manner of separating these components is to pass the mixture through what is called a cold acid extraction procedure wherein the stream is fed into a bath of concentrated sulfuric acid. Separation is achieved by virtue of the solubility of the isobutene in the sulfuric acid, the n-butenes and other hydrocarbons present passing overhead, for example as shown in U.S. Pat. Nos. 3,546,317 and 3,823,198.

Other processes have used various catalysts for converting the isobutene to diisobutene which is then easily separated from the product stream. For example, a process using a molecular sieve and elevated temperatures is disclosed in U.S. Pat. Nos. 3,531,539; 3,518,323 employs a supported nickel oxide catalyst; and 3,832,418 employs a Group VI or VIII metal deposited on acidic, amorphous silica-alumina in the same manner.

More recently, U.S. Pat. No. 4,215,011 disclosed the use of acid cation exchange resin in a heterogenous combination reaction-distillation system for the selective dimerization of isobutene in the presence of normal butenes. Although some codimer between n-butenes and isobutene are formed, the reaction is highly preferential for the reaction of isobutene with itself and provides a means to separate isobutene from a $C_4$ stream with little loss of other normal butenes.

Although the present process is suited to treat other isoolefin-normal olefins mixtures, it is of particular significance for the recovery of product streams with sufficiently low levels of isobutene to be processable to obtain useable n-butenes and particularly butene-1 which is the n-butene isomer employed in homopolymerization to produce polybutene or copolymerization with other monomers and as the preferred feed for oxidative dehydrogenation to produce butadiene-1,3.

The present process relates to fixed bed liquid phase systems wherein the isobutene is removed from a feed stream and a oligomer product of the isobutene recovered. In the prior liquid phase systems, the oligomerization is not easily controlled and in addition to diisobutene higher oligomers are produced, some of which form deposits on the resin catalyst reducing its effectiveness. Furthermore, the production of higher oligomers reduces the amount of the desired diisobutene. The diisobutene is preferred, since it is used for alkylations and is also useful as a gasoline blending stock, whereas the other lower oligomers, i.e., trimers and tetramers are not used for the alkylation and are no better as gasoline blending stock than the dimer.

It is a principal feature of the present process that the amount of isobutene in the stream is reduced to levels sufficiently low to allow further separation of a useful butene-1 product. It is another feature of the present process that a diisobutene production is enhanced compared to other possible oligomers.

It is an advantage of the present invention that a method of suppressing the formation of higher oligomers and polymers has been found in the process of separating isobutene from a $C_4$ hydrocarbon stream by oligomering the isobutene. It is a particular advantage of the present invention that the dimerization reaction of isobutene is enhanced.

It is a feature of the present invention that enhancement and suppression, respectively are obtained by the addition of a small amount of a relatively non-contaminating material to the reaction system.

Another feature of the present process is the substantial energy saving over the cold acid method of isobutene removal.

These and other features and advantages will become clearer from the following.

SUMMARY OF THE INVENTION

Briefly, the present invention is the discovery that the inclusion of a small amount of methyl tertiary butyl ether (MTBE) in a feed containing isobutene and other $C_4$, particularly n-butenes to a reactor containing a fixed bed cation ion exchange resin for reacting the isobutene to form oligomers in a liquid phase process for separating the isobutene from the other components of the feeds, enhances the dimerization of isobutene while suppressing the further reaction of isobutene to form higher oligomers or polymers.

The resultant product stream contains the isobutene dimers oligomers product, unreacted $C_4$'s and some MTBE. This stream is normally fractionated, e.g., by distillation to recover the unreacted $C_4$'s as an overhead fraction and the oligomer and MTBE as a bottoms. If the presence of MTBE is not desired in the oligomer fraction, a further distillation may be carried out or the first distillation may be carried out with an intermediate draw stream in the distillation column to recover a stream high in MTBE and containing some oligomer which can be recycled to the oligomerization reaction.

The oligomer reaction is exothermic and means to control the temperature in the catalyst bed are provided such as heat exchange means or the dilution of the feed stream with inerts.

It should be appreciated that in a feed stream having a low concentration of isobutene the reaction may be cooled too effectively by the other components of the feed stream and, it may actually be necessary to add heat to the reaction via the heat exchangers or by preheating the feed.

The preferred temperature of the reaction in the catalyst bed is in the range of 35° to 160° C., preferably 100° C. The higher temperatures favor the reaction of isobutene, and under normal conditions favor the oligomerization as well as side reactions such as copolymerization of n-butenes with the isobutene, however, the MTBE also tends to suppress the oligomerization (polymerization beyond the dimer) and the side reactions also. The mechanism by which the advantageous result of the present invention is obtained, is not known. That is, whether the MTBE, effects the catalyst to moderate its activity or enters into some reaction to stop the secondary oligomerizations is not known. It is fortuitous that the MTBE is detrimental only to the undesirable secondary oligomerization, whereby the dimerization of isobutene is actually enhanced.

The term "oligomer" is used herein to mean lower polymers of isobutene having greater than eight carbon atoms.

DETAILED DESCRIPTION OF THE INVENTION

The feed to the catalyst bed in the reactor may comprise up to 100 percent of the hydrocarbon feed to the reactor generally 5 to 100 mole % isobutene however, usually there will be other components of such a stream such as butene-1, butene-2, normal butane and isobutene, and the isobutene will comprise from about 9 to 60 mole % of the stream. Small amounts generally less than 1 mole % of the total stream may be $C_3$ and $C_5$ hydrocarbon, although now a refinery $C_4$ cut will be able to exclude the lower and higher hydrocarbons.

The amount of MTBE is small, usually an amount of at least 0.001 mole and no more than 1 mole per mole of isobutene in the feed stream to obtain the desired result. However, it is preferred that an amount in the range of 0.005 to 0.05 mole MTBE per mole of isobutene be used.

The residence time of the feed in the catalyst bed in conjunction with the temperature may be adjusted to maximize the isobutene removal or dimerization with the range of 0.1 to 10.0 liquid hourly space velocity (LHSV) which means the liquid volumes of hydrocarbon per volume of reactor containing catalyst per hour. Preferably, the LHSV will be in the range of 0.5 to 4.0, which would represent a moderately sized reactor with good unit productivity. It is appreciated that shorter residences times represent the feed throughput. Although it may be most advantageous to have small or moderate sized units, and high throughput, it would not be unreasonable to have a very large reactor with a low LHSV to obtain a feasible throughput.

The pressure employed in the reactor is that sufficient to maintain the liquid phase under the temperature condition employed, which will generally be from about 16 to 25 atmospheres.

Catalysts suitable for the present process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: Styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds. or by crosslinking with polyvinyl compounds; for example, with divinyl benzene, divinyl toluene, divinylphenylether and others. The polymers may be prepared in the presence of absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain sufficient sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly divinyl compounds, in which the polyvinyl benzene content is preferably 1 to 20% by weight of the copolymer (see, for example, German Patent Specification No. 908,247).

The ion exchange resin is preferably used in a granular size of about 0.25 to 1 mm, although particles from 0.15 mm up to about 1 mm may be employed. The finer catalysts provide high surface area, but also result in high pressure drops through the reactor. The macroreticular form of these catalysts is preferred because of the much larger surface area exposed and the limited swelling which all of these resins undergo in a non-aqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. Nos. 3,784,399; 3,770,567 and 3,849,243.

The catalyst may be packed into the reactor in bulk, in tubes or in the catalyst structures described in U.S. Pat. No. 4,215,011. The reactor may be horizontal, inclined or vertical. The fractionation of the product stream is entirely conventional, including the recovery and recycle of a part of the product stream to the reaction.

Referring now to the drawing, one mode of operation will be described. The reactor 10 is a vertical stainless steel tubular reactor with the resin catalyst bed 11 supported through the middle portion. The hydrocarbon product is removed via line 12. The stream 12 is split and a portion 13 is sent for storage or processing to recover isobutene dimer and unreacted isobutene for recycle (not shown) to line 18 which is the isobutene feed. A portion of the hydrocarbon product from line 12 passes via 15 for recycle to mix with incoming isobutene feed 18. This stream 15 contains dimer, unreacted isobutene and some MTBE (also other by-products).

The isobutene feed 18 passes through a heat exchange 19 where its temperature is adjusted usually by heating and hence, into the recycle line 15. (Note the heating of feed 18 and cooling of recycle 15 may be carried out as the same step by direct or indirect contacting of the two). Make up MTBE is added via 20 to the combined streams 18 and 15. The three streams (fresh feed, and recycle) pass through static mixer 17 into the reactor 10 and down through the resin bed 11. The recycle stream is pumped by pump 14 into recycle line 15 which passes through heat exchanger recycle line 15 which passes through heat exchanger 16 where it is cooled (note above). One startup, the heat exchanger 16 may be used to heat the recycle. Other items of standard equipment are not shown, but would be employed as obviously desirable or necessary, e.g., safety valves, liquid level indicators, drains, vents, etc.

Other means of controlling the reaction temperature rather than recycle of a portion of the product stream, such as the use of a tubular reactor with a heat exchange medium surrounding the tubes containing the catalyst or other conventional heat exchangers located in the reactor may be employed.

I claim:

1. In a liquid process for separating isobutene from a stream containing isobutene, and other hydrocarbons, comprising contacting said stream in liquid phase at a temperature in the range of 35° to 160° C. with a fixed bed cation exchange resin for a sufficient time to react at least a portion of the isobutene present therein with itself to form dimers and recovering a product stream containing said dimers and having a lower isobutene content than said feed stream whereby the formation of higher olegomers and codimers of isobutene with other olefins is suppressed, wherein the improvement comprises having said stream consists of isobutene, other hydrocarbons and a small amount of MTBE.

2. The process according to claim 1 wherein the temperature in in the range of 65° to 120° C.

3. The process according to claim 2 wherein the feed stream has an LHSV through the catalyst in the range of 0.1 to 10.0.

4. The process according to claim 3 wherein the LHSV is in the range of 0.5 to 4.0.

5. The process according to claim 1, 2 or 4 wherein the pressure during said contacting is in the range of 2 to 25 atmospheres.

6. The process according to claim 1 wherein from 0.001 to 1 mole per mole of isobutene of MTBE is present in said feed stream.

7. The process according to claim 6 wherein from 0.005 to 0.05 mole per mole of isobutene of MTBE is present in said feed stream.

8. The process according to claim 1 wherein said product stream is distilled to separate oligomer therefrom.

9. The method of producing diisobutene from a stream containing isobutene while suppressing the formation of higher oligomers comprising, contacting a hydrocarbon feedstream consisting of from 9 to 60 mole % isobutene, other hydrocarbons and 0.005 to 1 mole of MTBE per mole of isobutene in liquid phase at a temperature in the range of 65° to 120° C. cation exchange resin in a fixed bed for a sufficient time to react a portion of said isobutene and recovering a product stream containing diisobutene and MTBE.

10. The method according to claim 9 wherein said product stream is distilled to separate diisobutene therefrom.

11. The method according to claim 10 wherein the hydrocarbon feed stream is $C_4$ hydrocarbon.

12. The method according to claim 10 wherein a diisobutene fraction containing MTBE is recycled to said catalyst bed.

13. The method according to claim 9 wherein the MTBE is present in the mole ratio of 0.005 to 0.05 mole per mole of isobutene.

* * * * *